United States Patent
Williams et al.

(10) Patent No.: US 10,039,549 B2
(45) Date of Patent: Aug. 7, 2018

(54) LOADING UNIT RETENTION CLIP FOR SURGICAL STAPLING INSTRUMENT

(71) Applicant: Covidien LP, Mansfield, MA (US)

(72) Inventors: Justin Williams, Southbury, CT (US); Paul A. Scirica, Huntington, CT (US)

(73) Assignee: Covidien LP, Mansfield, MA (US)

(*) Notice: Subject to any disclaimer, the term of this patent is extended or adjusted under 35 U.S.C. 154(b) by 477 days.

(21) Appl. No.: 14/886,232

(22) Filed: Oct. 19, 2015

(65) Prior Publication Data
US 2016/0192934 A1    Jul. 7, 2016

Related U.S. Application Data

(60) Provisional application No. 62/100,512, filed on Jan. 7, 2015.

(51) Int. Cl.
| | |
|---|---|
| *A61B 17/04* | (2006.01) |
| *A61B 17/10* | (2006.01) |
| *A61B 17/072* | (2006.01) |
| *A61B 17/068* | (2006.01) |
| *A61B 17/115* | (2006.01) |
| A61B 17/00 | (2006.01) |

(52) U.S. Cl.
CPC .......... *A61B 17/105* (2013.01); *A61B 17/068* (2013.01); *A61B 17/1155* (2013.01); *A61B 2017/0046* (2013.01); *A61B 2017/0053* (2013.01); *A61B 2017/00473* (2013.01)

(58) Field of Classification Search
CPC .............. A61B 17/068; A61B 17/1155; A61B 2017/00477; A61B 17/105

USPC .... 227/175.1–182.1; 606/139, 153–154, 219
See application file for complete search history.

(56) References Cited

U.S. PATENT DOCUMENTS

| | | | | |
|---|---|---|---|---|
| 2,110,397 | A | * | 3/1938 | Kangas ................. E21B 17/046 279/76 |
| 2,304,038 | A | * | 12/1942 | Thompson .......... B25B 23/0035 279/79 |
| 3,193,165 | A | | 7/1965 | Akhalaya et al. |
| 3,388,847 | A | | 6/1968 | Kasulin et al. |
| 3,552,626 | A | | 1/1971 | Astafiev et al. |

(Continued)

FOREIGN PATENT DOCUMENTS

| | | |
|---|---|---|
| CA | 908529 A | 8/1972 |
| CN | 201481477 U | 5/2010 |

(Continued)

OTHER PUBLICATIONS

Partial European Search Report dated Jan. 16, 2017, issued in EP Appln. No. 16180339.

(Continued)

*Primary Examiner* — Robert Long

(57) ABSTRACT

A loading unit and retention clip assembly include a shell and a resilient retention clip. The shell has a proximal end portion and includes an annular surface that defines engagement openings. The retention clip is disposed about the annular surface of the proximal end portion. The retention clip has ends and a body between the ends. The retention clip has a lug positioned adjacent to each end of the body that extends inward from the body. Each lug is configured to extend through the engagement openings of the proximal end portion of the shell to releasably couple the shell to a surgical instrument.

8 Claims, 9 Drawing Sheets

(56) References Cited

U.S. PATENT DOCUMENTS

| | | |
|---|---|---|
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,569,133 A * | 2/1986 | Schmidt ............ A61B 17/32093 30/293 |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,647,241 A * | 3/1987 | Weber .................. F16B 7/0426 403/18 |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |

(56) References Cited

U.S. PATENT DOCUMENTS

| | | |
|---|---|---|
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |

(56) References Cited

U.S. PATENT DOCUMENTS

| | | |
|---|---|---|
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,826,976 B2 * | 11/2017 | Parihar .............. A61B 17/068 |
| 2003/0111507 A1 | 6/2003 | Nunez |
| 2004/0059227 A1 | 3/2004 | Nita et al. |
| 2004/0194324 A1 | 10/2004 | Youn-Chyuan |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0179375 A1 | 7/2008 | Scirica |
| 2008/0308605 A1 | 12/2008 | Scirica |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0326540 A1 | 12/2009 | Estes |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0186614 A1 | 8/2011 | Kasvikis |
| 2011/0192882 A1 | 8/2011 | Hess et al. |
| 2011/0276036 A1 | 11/2011 | Spranger et al. |
| 2012/0061448 A1 | 3/2012 | Zingman |
| 2012/0104071 A1 * | 5/2012 | Bryant .............. A61B 17/07207 227/175.1 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |

(56) References Cited

U.S. PATENT DOCUMENTS

| | | |
|---|---|---|
| 2013/0056516 A1 | 3/2013 | Viola |
| 2013/0060258 A1 | 3/2013 | Giacomantonio |
| 2013/0096591 A1 | 4/2013 | Hart et al. |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0123705 A1 | 5/2013 | Holm et al. |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181029 A1 | 7/2013 | Milliman |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0324978 A1* | 12/2013 | Nicholas ............ A61B 17/068 606/1 |
| 2014/0008413 A1 | 1/2014 | Williams |
| 2014/0012317 A1 | 1/2014 | Orban et al. |
| 2014/0305989 A1* | 10/2014 | Parihar ............ A61B 17/0686 227/176.1 |
| 2014/0305992 A1* | 10/2014 | Kimsey ............ A61B 17/068 227/176.1 |
| 2014/0309677 A1 | 10/2014 | Baldwin |
| 2015/0108201 A1 | 4/2015 | Williams |
| 2015/0320420 A1 | 11/2015 | Penna et al. |
| 2016/0192938 A1* | 7/2016 | Sgroi, Jr. ............ A61B 17/1155 227/175.1 |
| 2017/0020526 A1* | 1/2017 | Scirica ................ A61B 17/105 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 00282157 A1 | 9/1988 |
| EP | 0503689 A2 | 9/1992 |
| EP | 1190796 A1 | 3/2002 |
| EP | 1354560 A2 | 10/2003 |
| EP | 1631199 A1 | 3/2006 |
| EP | 2090245 A1 | 8/2009 |
| EP | 2524656 A2 | 11/2012 |
| EP | 2774549 A2 | 9/2014 |
| EP | 3042619 A1 | 7/2016 |
| FR | 1136020 A | 5/1957 |
| FR | 1461464 A | 2/1966 |
| FR | 1588250 A | 4/1970 |
| FR | 2243758 A1 | 4/1975 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9805261 A2 | 2/1998 |
| WO | 2001/054594 A1 | 8/2001 |
| WO | 2004107990 A1 | 12/2004 |
| WO | 2008/107918 A1 | 9/2008 |
| WO | 2012015917 A1 | 2/2012 |
| WO | 2014139327 A1 | 9/2014 |
| WO | 2014139440 A1 | 9/2014 |
| WO | 2014139442 A1 | 9/2014 |
| WO | 2014139467 A1 | 9/2014 |
| WO | 20140139442 A1 | 9/2014 |

OTHER PUBLICATIONS

European Search Report dated Nov. 30, 2016, issued in EP Application No. 16181395.
U.S. Appl. No. 62/100,512, filed Jan. 7, 2015, inventor: Williams et al.
U.S. Appl. No. 62/150,913, filed Apr. 22, 2015, inventor: Penna et al.
U.S. Appl. No. 14/591,193, filed Jan. 7, 2015, inventor: Sgroi, Jr.
U.S. Appl. No. 14/810,811, filed Jul. 28, 2015, inventor: Sgroi, Jr., et al.
U.S. Appl. No. 14/805,547, filed Jul. 22, 2015, inventor: Scirica, et al.
U.S. Appl. No. 14/859,590, filed Sep. 21, 2015, inventor: Sgroi.
U.S. Appl. No. 14/804,814, filed Jul. 21, 2015, inventor: Williams et al.
European Search Report dated May 10, 2016, issueed in EP Application No. 15198203.
European Search Report dated May 17, 2016, issued in EP Application No. 16150284.
European Search Report dated Jun. 24, 2016, issued in EP Application No. 16150288.5.
EP Examination Report dated Jun. 20, 2017, issued in EP Application No. 16150288.
European Search Report dated May 23, 2017, issued in EP Application No. 16189648.
European Search Report dated Sep. 1, 2016, issued in EP 16166326.

* cited by examiner

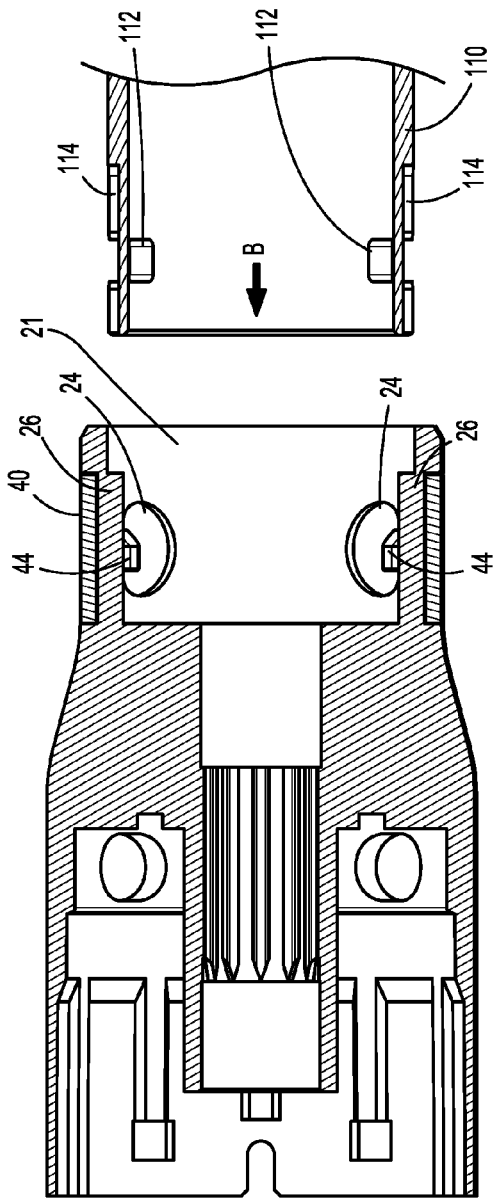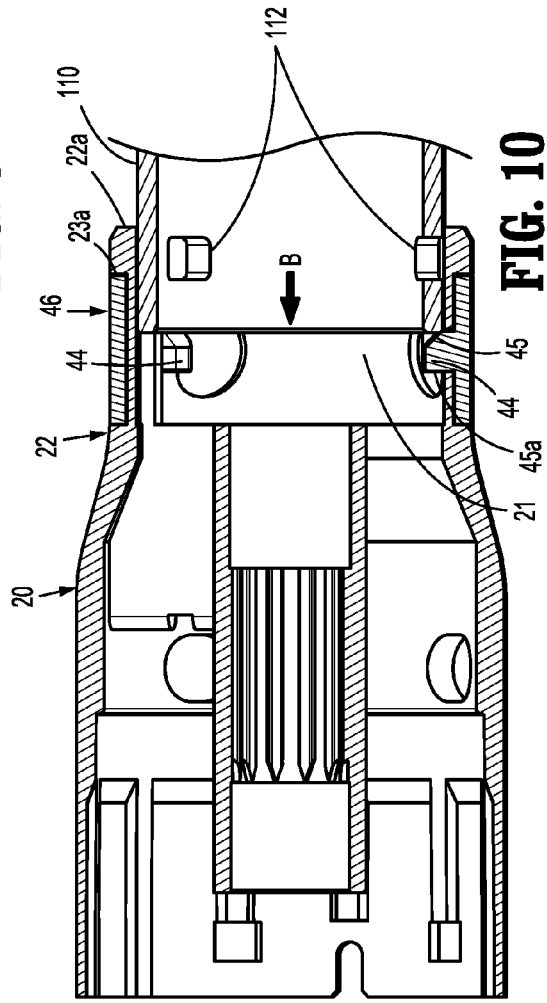
FIG. 9
FIG. 10

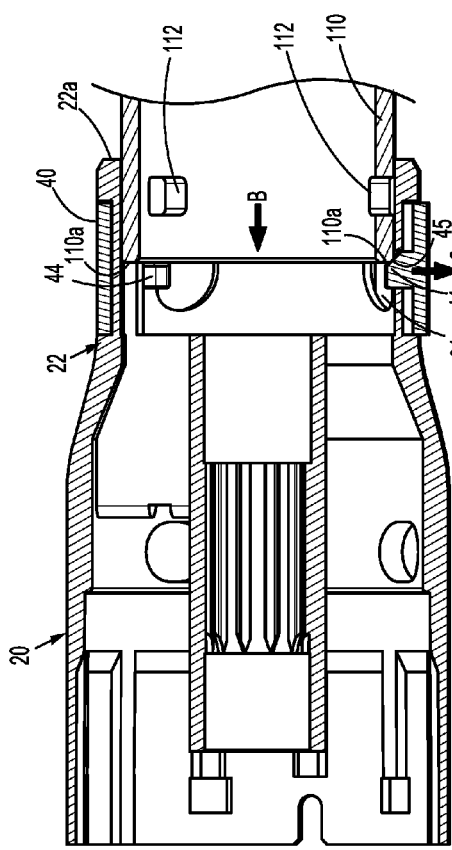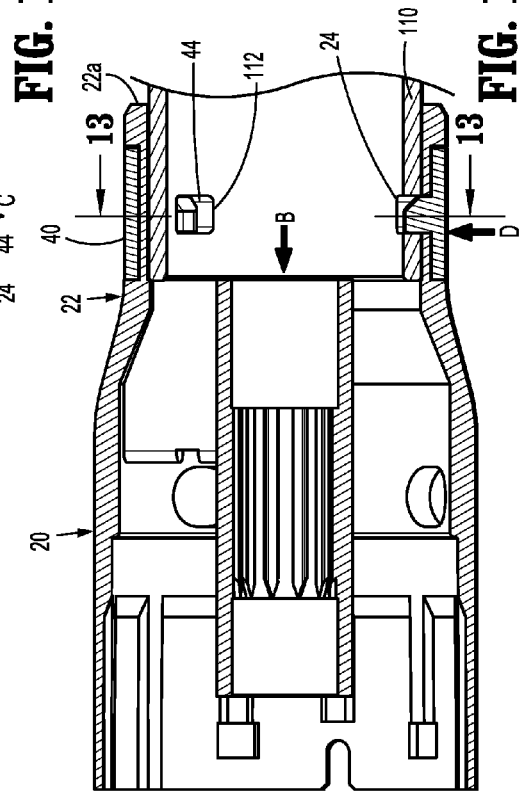

LOADING UNIT RETENTION CLIP FOR SURGICAL STAPLING INSTRUMENT

CROSS-REFERENCE TO RELATED APPLICATIONS

This application claims the benefit of and priority to U.S. Provisional Patent Application No. 62/100,512, filed Jan. 7, 2015, the entire disclosure of which is incorporated by reference herein.

BACKGROUND

1. Technical Field

The present disclosure relates generally to surgical stapling instruments. More specifically, the present disclosure relates to circular stapling instruments having replaceable loading units.

2. Background of Related Art

Surgical stapling instruments configured to join tissue portions during a surgical procedure are well known. These instruments include linear end effectors which are oriented parallel or transverse to a longitudinal axis of the instrument. These instruments also include circular end effectors. Typically, the linear stapling instruments include a disposable loading unit or a replaceable cartridge that allows the stapling instrument to be used multiple times. In contrast, conventional circular stapling instruments typically include a cartridge or shell assembly that is fixedly attached to the instrument such that the instrument must be disposed of after a single use.

A need exists in the art for a simple, inexpensive instrument for releasably, but securely, fastening a cartridge or shell assembly to a circular stapling instrument to facilitate reuse of the stapling instrument.

SUMMARY

In an aspect of the present disclosure, a loading unit and retention clip assembly include a shell and a resilient retention clip. The shell has a proximal end portion and includes an annular surface that defines engagement openings. The retention clip is disposed about the annular surface of the proximal end portion. The retention clip has ends and a body between the ends. The retention clip has a lug positioned adjacent to each end of the body that extends inward from the body. Each lug is configured to extend through the engagement openings of the proximal end portion of the shell to releasably couple the shell to a surgical instrument. The loading unit may be configured to receive a staple cartridge.

In aspects, the annular surface defines an annular groove with the proximal end portion of the shell. The body of the retention clip may be disposed within the annular groove. The resilience of the body of the retention clip may urge the lugs towards one another.

In some aspects, the retention clip includes a key that extends radially inward from the body between the ends which is configured to radially align the retention clip with the proximal end portion of the shell. The annular surface may define a key slot for receiving the key therethrough. The key slot may be longitudinally spaced apart from a proximal end of the shell. The key may retain the retention clip to the proximal end portion by an interference fit with walls defining the key slot. The key may include a leg and a key end. A first end of the leg may be coupled to the body and a second end of the leg may extend towards the longitudinal axis of the shell. The key end may be positioned at the second end of the leg. The leg may be sized to freely slide within the key slot and the key end may be sized to retain the leg within the key slot.

In certain aspects, each engagement opening includes a lug portion and an enlarged portion. The lug portion of each engagement opening is sized to receive one of the lugs of the retention clip. The enlarged portion of each engagement opening may be sized and positioned to receive a finger of a user when a lug is received with the lug portion of the respective engagement opening.

In another aspect of the present disclosure, a surgical instrument and loading unit assembly includes a loading unit, a surgical instrument, and a resilient retention clip. The loading unit includes a shell that has a proximal end portion. The proximal end portion includes an annular surface that defines engagement openings. The surgical instrument has a distal end that is received within the proximal end portion of the shell. The retention clip is disposed about the annular surface of the proximal end portion of the shell. The retention clip has ends and a body positioned between the ends. The retention clip has a lug positioned adjacent to each end of the body that extends inward from the body. Each lug extends through the engagement openings of the proximal end portion of the shell to releasably couple the loading unit to the surgical instrument.

In aspects, the distal end of the surgical instrument defines a key way that extends therethrough. The retention clip may include a key extending inward from that body which is received in the key way to radially align the distal end of the surgical instrument with the loading unit.

In some aspects, the surgical instrument defines windows that extend through the distal end of the surgical instrument. The lugs may be received by the windows of the surgical instrument to releasably couple the loading unit to the surgical instrument. An outer surface of the surgical instrument may define grooves that extend parallel to the longitudinal axis of the surgical instrument. The proximal end of the shell may include ribs that extend inward which are received within the grooves to radially fix the loading unit relative to the surgical instrument. Each of the grooves may be positioned in communication with a respective one of the windows. Each of the grooves may be positioned closer to the key way relative to the respective one of the windows. Each of the grooves may extend through the distal end of the surgical instrument.

In another aspect of the present disclosure, a method of securing a loading unit to a surgical instrument includes inserting a distal end of the surgical instrument into a proximal end portion of the loading unit. The distal end of the surgical instrument flexing lugs of a retention clip that pass through engagement openings defined in an annular surface of the loading unit outward as the distal end of the surgical instrument is received within the proximal end portion of the loading unit. The lugs are received in windows defined in the distal end of the surgical instrument when the distal end of the surgical instrument is fully received within the proximal end portion of the loading unit to secure the loading unit to the surgical instrument.

In aspects, method may include attaching the retention clip to the proximal end portion of the loading unit. Attaching the retention clip to the proximal end portion of the loading unit may precede inserting a distal end of the surgical instrument into the proximal end portion of the loading unit.

In some aspects, attaching the retention clip to the proximal end portion of the loading unit includes inserting a key of the retention clip through a key slot defined in the annular surface of the loading unit and positioning a body of the retention clip within an annular groove defined in the proximal end portion of the loading unit until each lug passes through a respective engagement opening defined in the annular surface. Inserting the key of the retention clip through the key slot may include press-fitting the key into the key slot. Inserting the key of the retention clip through the key slot may include positioning a key end of the key radially inward from the annular surface. The key end may retain the retention clip to the proximal end portion of the loading unit.

In certain aspects, the method includes aligning the distal end of the surgical instrument with a proximal end portion of the loading unit such that a key of the retention clip is aligned with a key way that extends through the distal end of the surgical instrument. Inserting the distal end of the surgical instrument into a proximal end portion of the loading unit may include sliding the key of the retention clip into the key way of the distal end of the surgical instrument.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 9 is a cross-sectional view of the loading unit taken along the section line 9-9 of FIG. 8 with the distal end of the adapter of FIG. 3 aligned with the loading unit;

FIG. 10 is a cross-sectional view of the loading unit taken along the section line 10-10 of FIG. 8 with the distal end of the adapter of FIG. 3 received in the proximal end portion of the loading unit;

FIG. 11 is a side cross-sectional view of the loading unit and adapter of FIG. 10 with a portion of the retention clip urged radially outward;

FIG. 12 is a side cross-sectional view of the loading unit and the adapter of FIG. 11 coupled together;

DETAILED DESCRIPTION OF EMBODIMENTS

Figure 1:
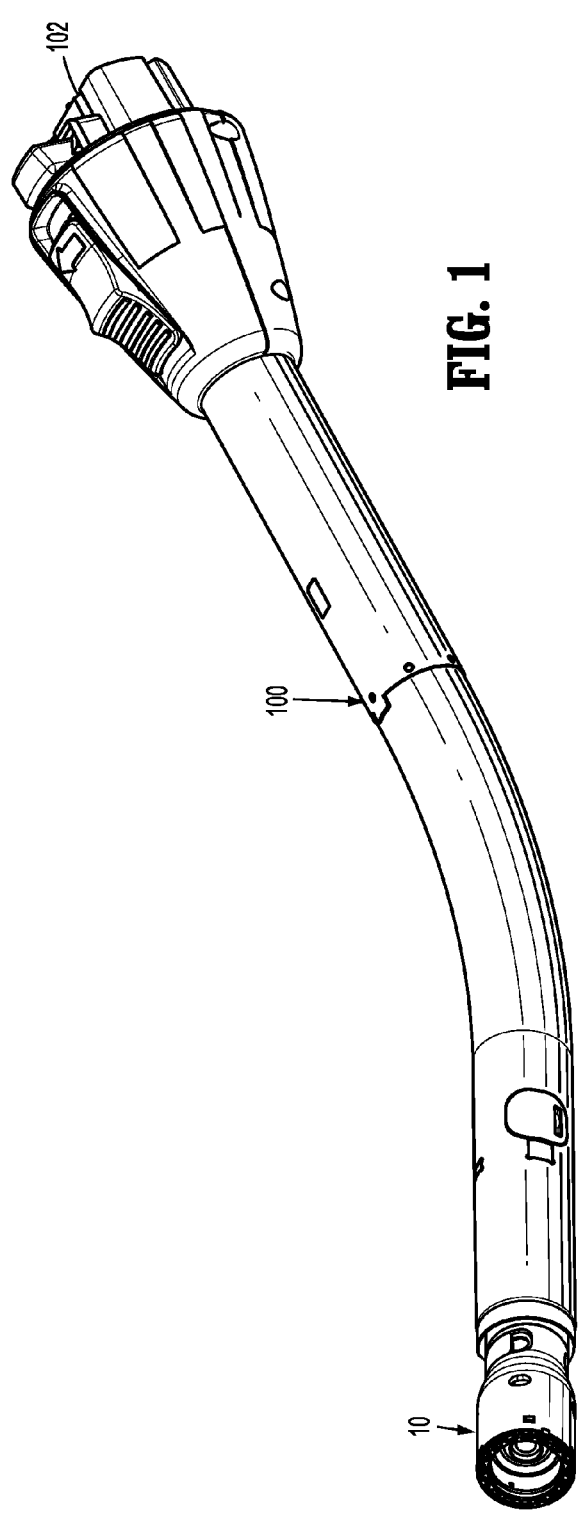
FIG. 1 is a perspective view of a circular stapling adapter and a loading unit in accordance with the present disclosure with the loading unit releasably coupled to a distal end of the adapter.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 2:
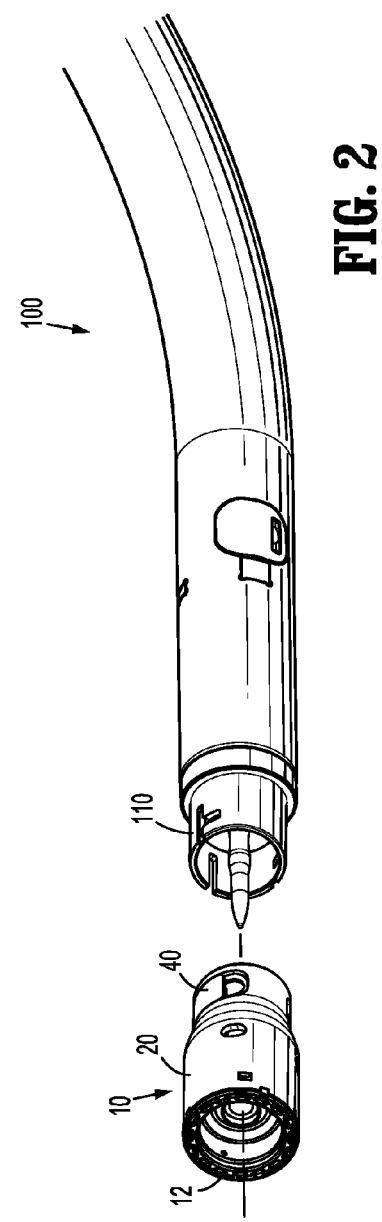
FIG. 2 is a perspective view of the adapter and loading unit of FIG. 1 with the loading unit decoupled from the adapter.

FIGS. 1 and 2 illustrate a loading unit 10 and an adapter 100 in accordance with an embodiment of the present disclosure. The loading unit 10 is configured for selective connection to a powered hand held electromechanical instrument (not shown) via the adapter 100. Alternatively, the loading unit 10 can be configured for connection to a manually actuated handle assembly or stapling instrument such as described in U.S. Pat. No. 8,789,737 ("the '737 Patent"), which is incorporated herein by reference. In such an embodiment, an elongated body portion of the stapling instrument may have a configuration similar to that of the adapter 100 as shown in FIG. 2. In the illustrated embodiment, the loading unit 10 is releasably coupled to a distal end portion 110 of the adapter 100 and includes a staple cartridge 12, a shell assembly 20, and an attachment member or retention band 40 for releasably securing the loading unit 10 to the adapter 100. The loading unit 10 may also include an anvil (not shown). The adapter 100 is configured to translate movement of a stapling instrument, e.g., an electromechanical instrument (not shown), to actuate the staple cartridge 12 to suture and cut tissue (not shown). A proximal end 102 of the adapter 100 is attachable to the stapling instrument to actuate the staple cartridge 12. It is contemplated that the proximal end 102 of the adapter 100 may be attached to a manually actuated instrument such as described in the '737 Patent to actuate the staple cartridge 12.

For a detailed description of the structure and function of an exemplary adapter and loading unit, please refer to commonly owned U.S. Provisional Patent Application Ser. No. 62/066,518 filed Oct. 21, 2014. For a detailed description of the structure and function of an exemplary electromechanical instrument, please refer to commonly owned U.S. patent application Ser. No. 13/484,975, filed on May 31, 2012, now published as U.S. Patent Publication No. 2012/0253329. Each of these applications is incorporated herein by reference in its entirety.

Figure 3:
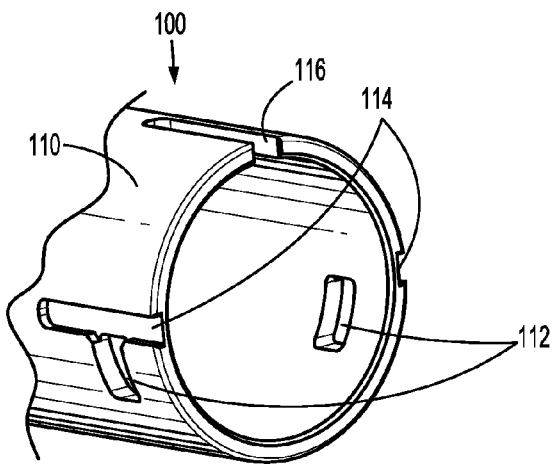
FIG. 3 is an enlarged perspective view of a portion of the distal end of the adapter of FIG. 2.

With reference to FIG. 3, the distal end portion 110 of the adapter 100 or surgical instrument defines windows 112, grooves 114, and a key way 116. The windows 112 extend through the distal end portion 110 of the adapter 100 and are spaced-apart from the distal end 110*a* of the adapter 100. The grooves 114 are defined in the outer surface of the distal end portion 110 of the adapter 100 and extend in a direction parallel to the longitudinal axis of the adapter 100. It is contemplated that the grooves 114 may define slots through the distal end portion 110 of the adapter 100.

The key way 116 extends through the distal end portion 110 of the adapter 100 in a direction parallel to the longitudinal axis of the adapter 100 and is positioned between the windows 112. As shown, the key way 116 is positioned half-way between the windows 112; however, it is contemplated that the key way 116 may be positioned closer to one of the windows 112 than to the other window 112. Each of the grooves 114 communicates with one of the windows 112 to form a "T" shaped configuration with the each groove 114 being positioned closer to the key way 116 than a respective window 112. However, it is contemplated that the grooves 114 may be spaced apart from or positioned through the windows 112. In addition, it is contemplated that the windows 112 may be positioned closer to the key way 116 than a respective groove 114.

Figure 4:
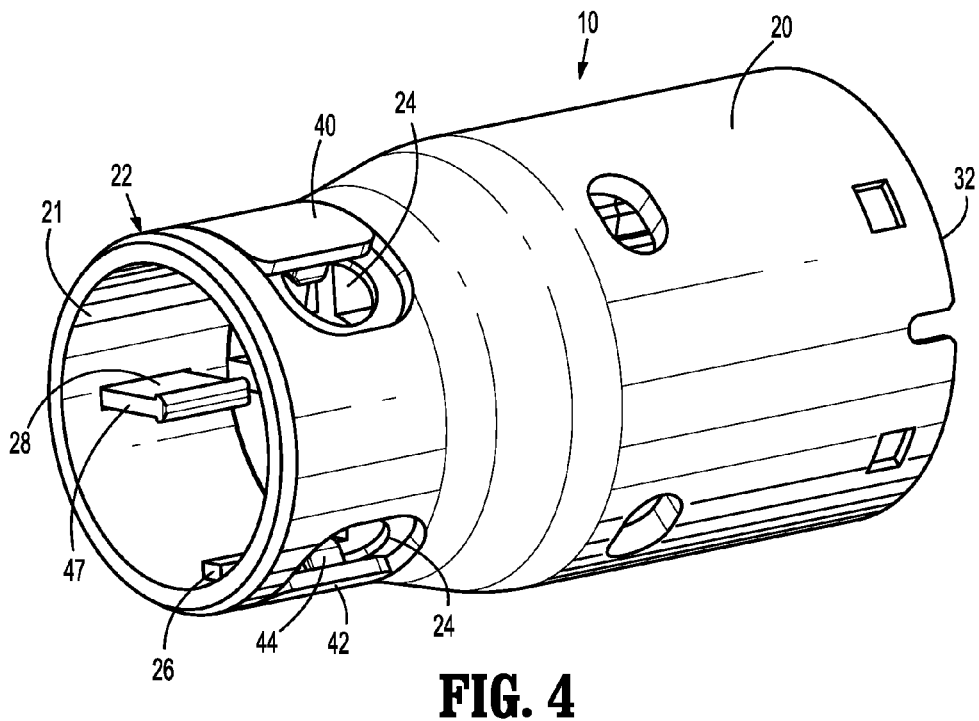
FIG. 4 is an enlarged perspective view of the loading unit of FIG. 2.
Figure 5:
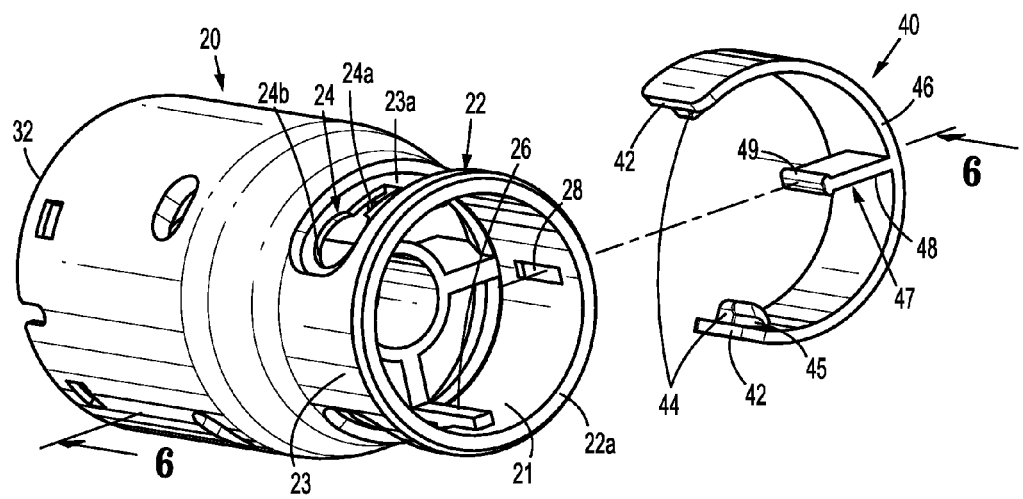
FIG. 5 is a perspective view of the loading unit of FIG. 3 with a retention clip separated from a shell assembly.
Figure 6:
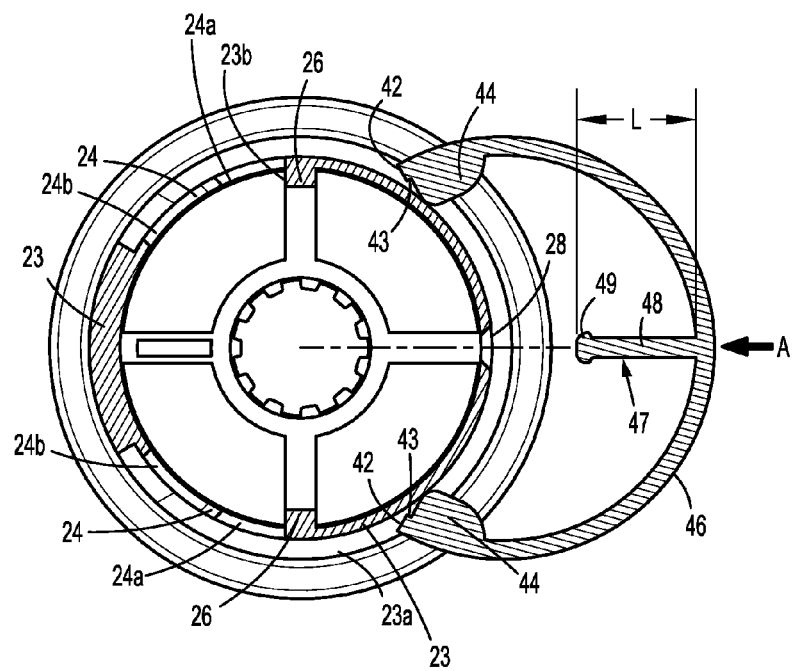
FIG. 6 is a cross-sectional view taken along the section line 6-6 of FIG. 5.

Referring to FIGS. 4-6, the shell assembly 20 includes a proximal end portion 22 that defines an opening 21 dimensioned and configured to receive the distal end portion 110 (FIG. 3) of the adapter 100 and a distal end 32 that defines a receptacle (not shown) for receiving and supporting the staple cartridge 12 (FIG. 2). The opening 21 has a shape which corresponds to the distal end portion 110 of the adapter 100. The proximal end portion 22 includes an annular surface 23 (FIG. 5) that defines engagement openings 24. Each of the engagement openings 24 includes a lug portion 24a and an enlarged portion 24b. The engagement openings 24 are spaced apart from one another about the annular surface 23 and orientated such that the lug portion 24a of one engagement opening 24 is positioned closer to the lug portion 24a of the other engagement portion than to the enlarged portion 24b of the other engagement opening 24. The annular surface 23 also defines a key slot 28 that is positioned between the engagement openings 24 and closer to the lug portions 24a of each of the engagement openings 24 than to the enlarged portions 24b. The inner surface of the proximal end portion 22 includes ribs 26 that protrude towards and in a direction parallel to the longitudinal axis of the shell assembly 20. The ribs 26 are positioned in opposition to one another adjacent the lug portions 24a of the engagement openings 24.

The annular surface 23 of the proximal end portion 22 of the shell assembly 20 defines an annular groove 23a that is dimensioned to receive the retention clip 40. As shown, the annular groove 23a extends along a portion of the annular surface 23 between the lug portions 24a of the engagement openings 24. Alternatively, it is contemplated that the annular groove 23a extends along the entire annular surface 23.

Figure 8:
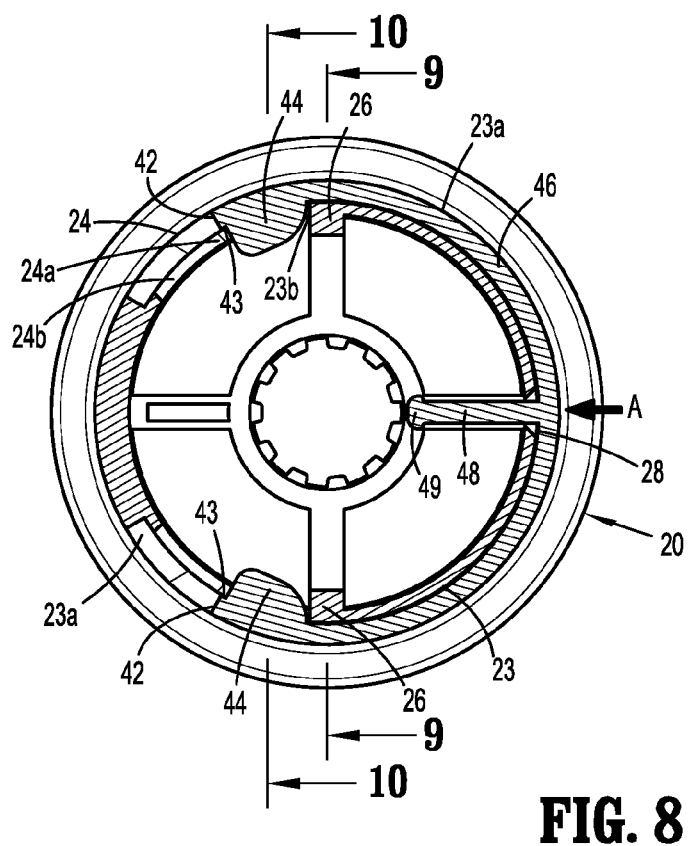
FIG. 8 is a cross-sectional view taken along the section line 8-8 of FIG. 7.

With continued reference to FIG. 5, the retention clip 40 includes ends 42 and a body 46 between the ends 42. The body 46 of the retention clip 40 defines a partial circular shape and is sized to be received within the annular groove 23a of the proximal end portion 22 (FIG. 8). The body 46 has an annular dimension of about 240°. Alternatively, the body 46 may have a variety of annular dimensions between about 181° and 360°. The body 46 is formed of a resilient material which is flexed outwardly when positioned about the proximal end portion 22 of the shell assembly 20. The body 46 is dimensioned such that the resilient nature of the body 46 biases the ends 42 of the body 46 towards one another to retain the body 46 on the proximal end portion 22. Each end 42 includes a lug 44 that protrudes from the inner surface of the retention clip 40 and is sized to be received within the lug portions 24a of the engagement openings 24.

The lugs 44 are positioned along the body 46 such that the body 46 has an annular dimension of at least 180° between the lugs 44. When the body 46 is positioned within the annular groove 23, the resilience of the body 46 urges the lugs 44 into the lug portions 24a of the engagement openings 24 to secure the retention clip 40 to the proximal end portion 22 of the shell assembly 20. The lugs 44 may be spaced apart from the ends 42 to define an engagement surface 43 between the lugs 44 and the ends 42 for selective engagement by a clinician to facilitate removal of the retention clip 40 from the proximal end portion 22 of the shell assembly 20 as detailed below.

The retention clip 40 includes a key 47 protruding from an inner surface of the body 46 between the lugs 44. The key 47 is sized and configured to pass through the key slot 28 in the annular surface 23 of the shell assembly 20. The key 47 includes a leg 48 that protrudes a length L (FIG. 6) to a key end 49. The key end 49 is sized larger than the leg 48 and must be pressed through the key slot 28 of the annular surface 23 of the shell assembly 20 during assembly of the loading unit 10 (FIG. 1) and the adapter 100. The key end 49 inhibits the key 47 from being withdrawn through the key slot 28 as detailed below. The leg 48 of the key 47 may have a constant width that permits the leg 48 to freely pass through the key slot 28. It is contemplated that the leg 48 may have constant width that is dimensioned to engage the walls defining the key slot 28 as the leg 48 is pressed through the key slot 28 to retain the key 47 within the key slot 28. Further, it is contemplated that the leg 48 may be tapered from a narrow width adjacent the key end 49 to a broad width adjacent the body 46 such that when the body 46 is fully disposed within the annular groove 23a, the key 47 engages with the walls defining the key slot 28 to inhibit withdrawal of the key 47 from the key slot 28 when the body 46 is disposed within the annular groove 23a.

Figure 7:
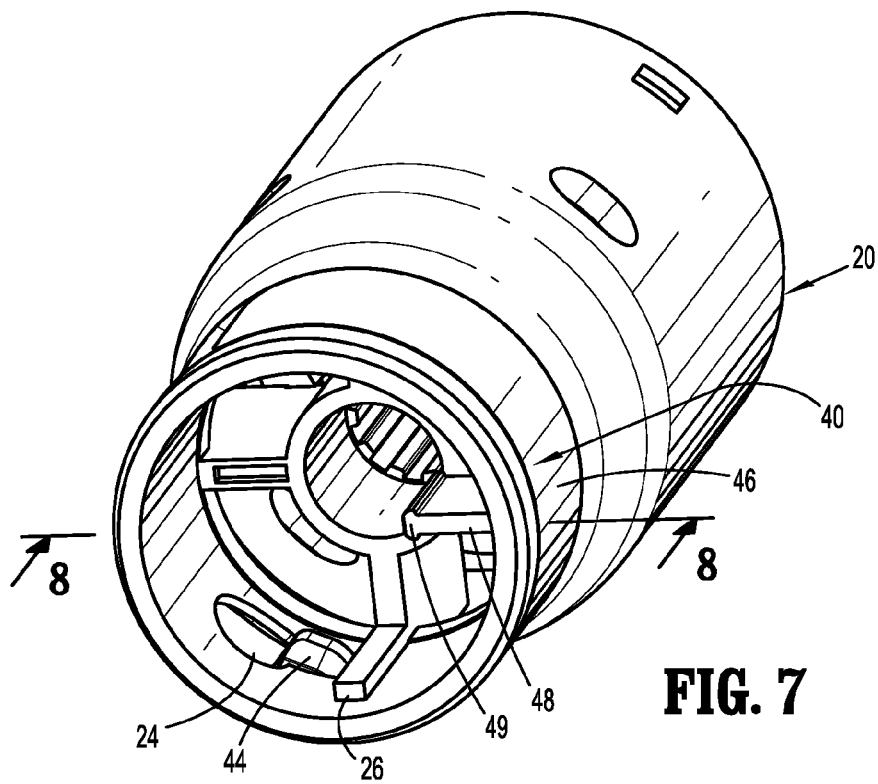
FIG. 7 is a rear perspective view of the loading unit of FIG. 4.

Referring now to FIGS. 6-8, a method of attaching the retention clip 40 to the shell assembly 20 in accordance with the present disclosure is disclosed. The retention clip 40 is positioned relative to the proximal end portion 22 of the shell assembly 20 such that the key 47 is aligned with the key slot 28. The retention clip 40 is then pressed over the proximal end portion 22 of the shell assembly 20 in a direction transverse to the longitudinal axis of the shell assembly 20 as represented by Arrow A (FIG. 6). As the retention clip 40 is pressed over the proximal end portion 22 of the shell assembly 20, the lugs 44 of the retention clip 40 engage the annular surface 23 of the shell assembly 20 such that the body 46 of the retention clip 40 flexes outwardly. The engagement of the key end 49 with the key slot 28 radially aligns the retention clip 40 with the shell assembly 20. Continued pressing of the retention clip 40 over the proximal end portion 22 of the shell assembly 20, presses the key end 49 through the key slot 28 such that the leg 48 is positioned within the key slot 28.

With particular reference to FIG. 8, the retention clip 40 is pressed onto the proximal end portion 22 until the body 46 of the retention clip 40 is fully received within the annular groove 23a. When the body 46 is fully received within the annular groove 23a, the lugs 44 are disposed within the lug portions 24a of the engagement openings 24. When the lugs 44 are disposed within the lug portions 24a, the lugs 44 engage the engagement surface 23b of the proximal end portion 22 of the shell assembly 20 to retain the retention clip 40 within the annular groove 23a. It is contemplated that the lugs 44 may engage the ribs 26 when the lugs 44 are disposed within the lug portions 24a.

As the retention clip 40 is pressed onto the proximal end portion 22 of the shell assembly 20, the leg 48 slides through the key slot 28. As detailed above, the leg 48 may be dimensioned to freely slide within key slot 28 of the proximal end portion 22 of the shell assembly or the leg 48 may be dimensioned to engage the inner walls defining the key slot 28 to help retain the retention clip 40 on the shell assembly 20. Alternatively, the leg 48 may be tapered and press fit through the key slot 28 to secure the retention clip 40 within the annular groove 23a such that when the body 46 of the retention clip 40 is received within or seated in the annular groove 23a, the leg 48 is in interference with the annular surface 23 to secure the retention clip 40 to the shell assembly 20. By securing the retention clip 40 to the shell assembly 20, the retention clip 40 is less likely to inadvertently become disengaged from the shell assembly 20 as the loading unit 10 is attached and detached from an adapter (e.g., adapter 100) as detailed below.

Referring now to FIGS. 9-14, to secure the loading unit 10 to the distal end 110 of the adapter 100 or an elongated body of a manually actuated surgical instrument after the retention clip 40 is secured to the shell assembly 20 the longitudinal axis of the shell assembly 20 is first aligned with the longitudinal axis of the adapter 100 as shown in FIG. 9. In addition, the proximal end portion 22 of the shell assembly 20 is radially aligned with the distal end portion 110 of the adapter 100 such that the ribs 26 of the shell assembly 20 are aligned with the grooves 114 of the adapter 100. It will be appreciated that when the ribs 26 are aligned with the grooves 114, the key slot 28 of the shell assembly 20 and leg 48 of the key are aligned with the key way 116 of the adapter 100. Further when the ribs 26 are aligned with the grooves 114, the windows 112 of the adapter 100 are also aligned with the engagement openings 24 of the shell assembly 20 (FIG. 9).

With the ribs 26 aligned with the grooves 114, the proximal end portion 22 of the shell assembly 20 is slid over the distal end portion 110 of the adapter 100 such that the distal end portion 110 is received within the opening 21 of the shell assembly 20 (FIG. 10). The adapter 100 is slid into the opening 21 of the shell assembly 20 until the distal end portion 110 of the adapter 100 engages the lugs 44 of the retention clip 40 that protrude through the engagement openings 24 of the shell assembly 20.

With reference to FIG. 11, when the distal end 110a of the adapter 100 engages the lugs 44 of the retention clip 40, the ends 42 of the retention clip 40 are moved away from the longitudinal axis of the shell assembly 20 as indicated by Arrow C such that the body 46 is flexed outward to permit the distal end portion 110 of the adapter 100 to slide into the shell assembly 20 until the windows 112 of the adapter 100 are longitudinally aligned with the engagement openings 24 of the shell assembly 20 (FIG. 12). It will be appreciated, that the distal end portion 110 of the adapter 100 may engage tapered surfaces 45 of the lugs 44 to cam the lugs 44 away from the longitudinal axis of the shell assembly 20 as the distal end portion 110 of the adapter 100 engages the tapered surfaces 45. When the windows 112 are aligned with the engagement openings 27, the lugs 44 extend through the engagement openings 24 of the shell assembly 20 snapping through the windows 112 of the adapter 100 to longitudinally fix the shell assembly 20 to the adapter 110. As illustrated in FIG. 12, the distal surface 45a of the lugs 44 can be substantially perpendicular in relation to the longitudinal axis of the shell assembly 20 to prevent the adapter 100 from being pulled from the shell assembly 20. It will be appreciated that the resilience and shape of the body 46 of the retention clip 40 and the position of the lugs 44 along the body 46 urge the lugs 44 through the windows 112 as indicated by Arrow D (FIG. 12).

Figure 13:
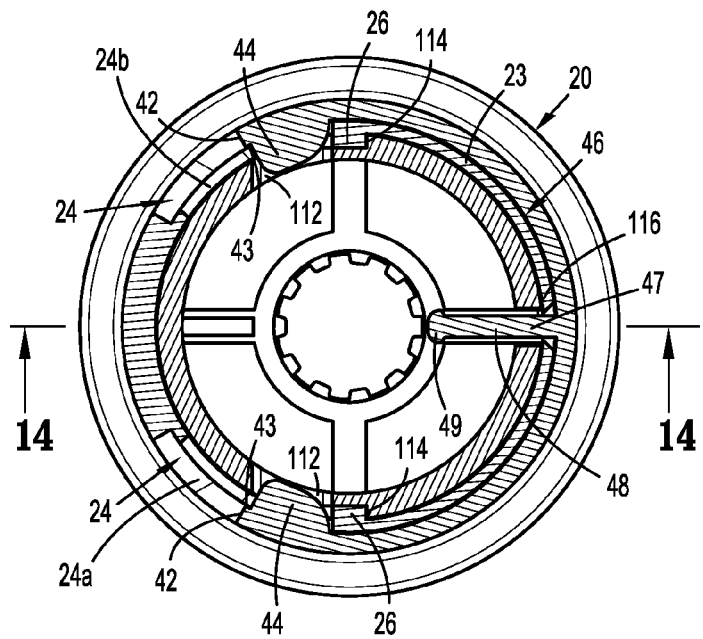
FIG. 13 is a rear cross-sectional view taken along the section line 13-13 of FIG. 12.
Figure 14:
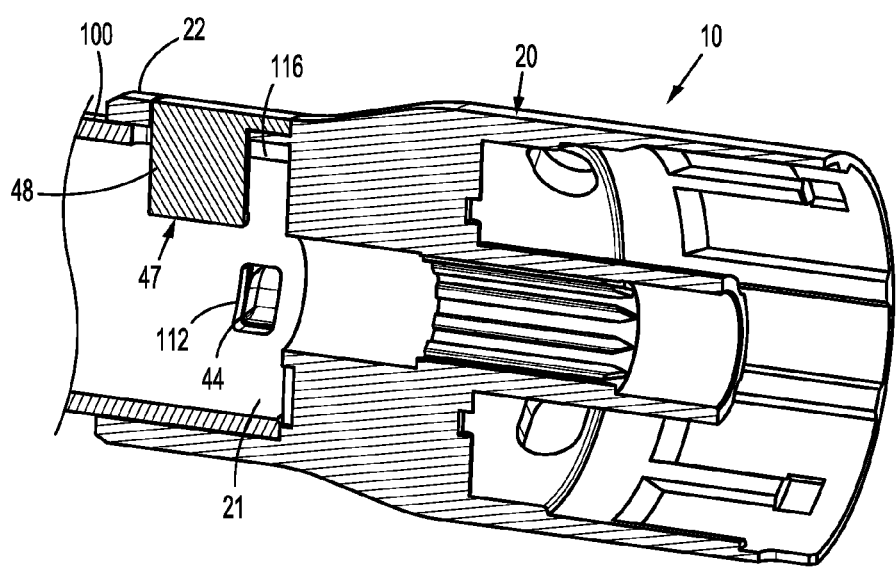
FIG. 14 is a cross-sectional view taken along the line 14-14 of FIG. 13.

With particular reference to FIGS. 13 and 14, when the ribs 26 are received within the grooves 114 to radially align the shell assembly 20 with the adapter 100, the key 47 is aligned with the key way 116 of the adapter 110. As the distal end portion 110 of the adapter 100 is slid into the opening 21 formed by the shell assembly 20, the key 47 slides into the key way 116 of the adapter 100.

With the loading unit secured to the adapter 100, the adapter 100 and loading unit 10 may be used to perform a surgical procedure. After surgical procedure is completed, the loading unit 10 can be released from the adapter 100 as detailed below. With the loading unit 10 separated from the adapter 100, the adapter 100 may be sterilized for reuse in another surgical procedure or attached to a new loading unit for use again in the ongoing surgical procedure. In addition, the loading unit 10 may be sterilized for use in another surgical procedure or may be discarded.

Referring to FIG. 13, the loading unit 10 is detached from the adapter 100, or an elongated body of a manually actuated surgical instrument, by moving the lugs 44 of the retention clip 40 out of the windows 112 of the adapter 100. As detailed above, the resilience of the body 46 urges the lugs 44 through the windows 112 as the windows 112 become aligned with the engagement openings 24. To move the lugs 44 out of the windows 112 and facilitate separation of the shell assembly 20 from the adapter 100, the ends 42 of the body 46 adjacent the lugs 44 are engaged to move the lugs 44 out of the windows 112. It will be appreciated that the enlarged portion 24b of the engagement opening 24 is sized to permit a finger of a clinician or a tool to access and engage the ends 42 of the retention clip 40 to manually flex the ends 42 of the retention clip 40 outwardly to lift the lugs 44 from the windows 112. As the lug 44 is removed from the window 112, the body 46 of the retention clip 40 is flexed. With the lugs 44 removed from the windows 112, the loading unit 10 is removed from the distal end portion 110 of the adapter 100 or an elongated body of a manually actuated surgical instrument.

In an alternative embodiment, one end 42 of the retention clip 40 may be flexed outwardly to permanently or plastically deform the body 46 to prevent the lug 44 from protruding into the window 112 of the adapter 100 when the retention clip 40 is released. The retention clip 40 may then be manipulated to remove the other lug 44 from within the window 112 of the adapter 100 to separate the shell assembly 20 from the adapter 100. The permanent deformation of the body 46 enables a clinician to remove the loading unit 10 from the adapter 100 without engaging both ends 42 of the retention clip 40 simultaneously.

Figure 15:
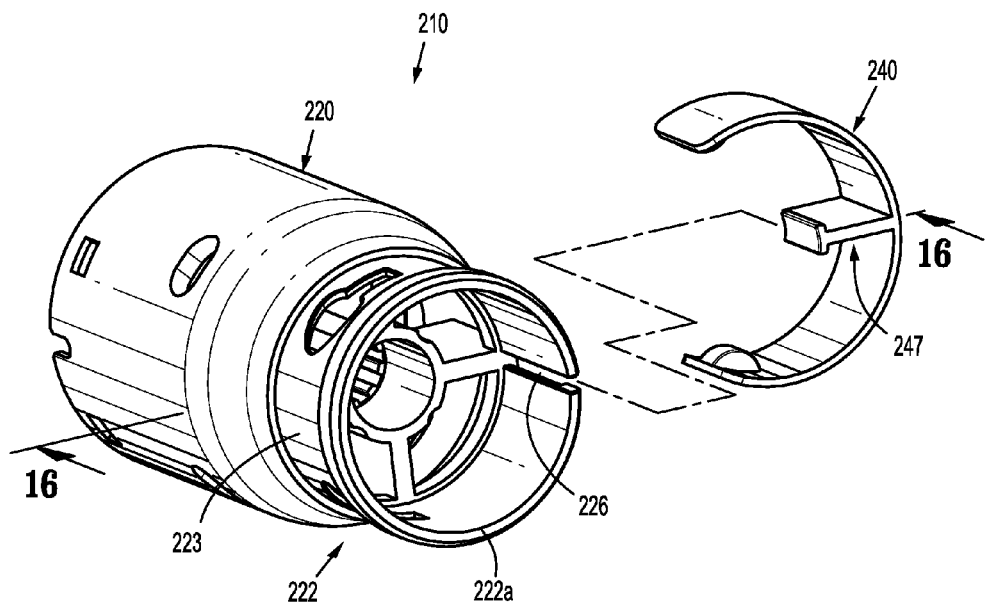
FIG. 15 is a rear perspective view of another loading unit provided in accordance with the present disclosure with a retention clip separated from a shell assembly.
Figure 16:
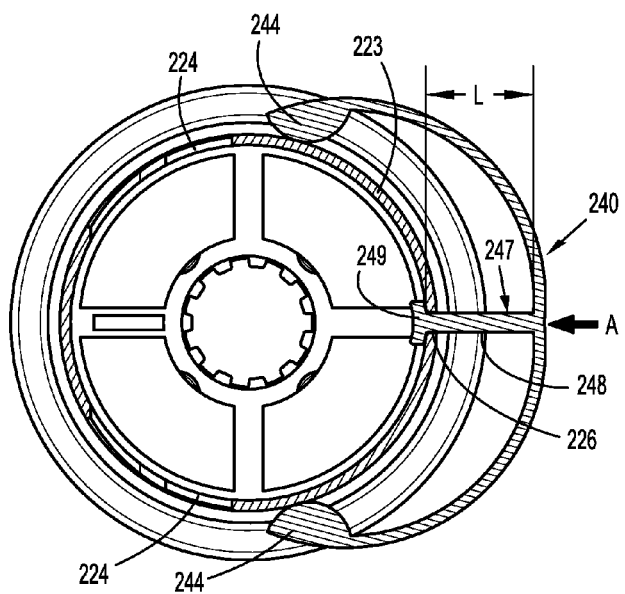
FIG. 16 is a rear cross-sectional view taken along the section line 16-16 of FIG. 15 with the retention clip engaging the shell assembly.
Figure 17:
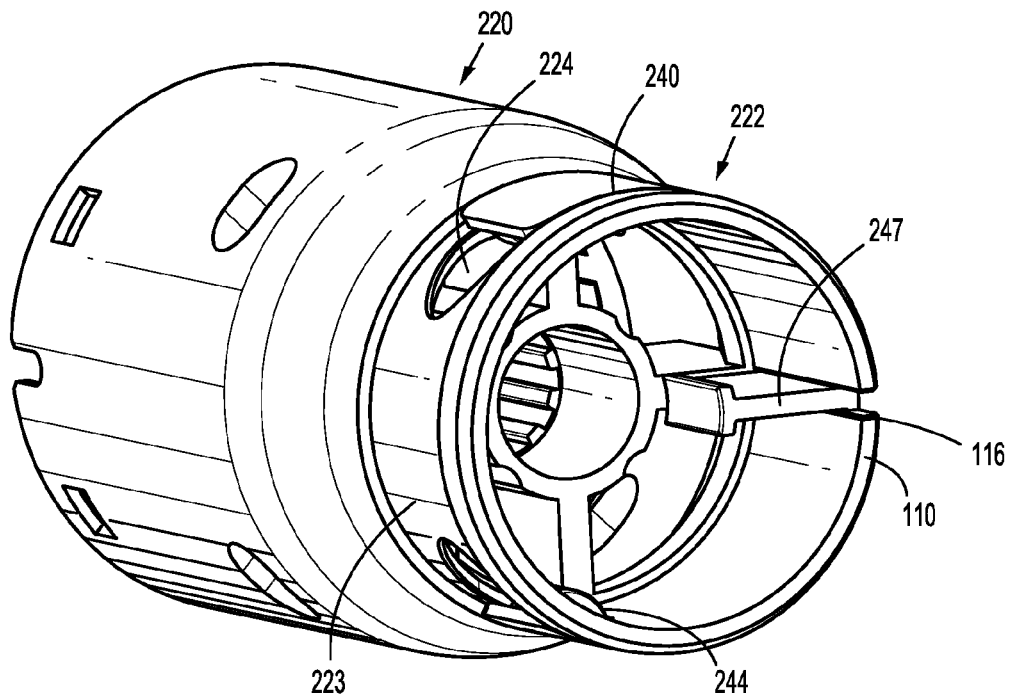
FIG. 17 is a rear perspective view of the assembled loading unit of FIG. 15.

With reference to FIG. 15, another loading unit 210 includes a shell assembly 220 and a retention clip 240. The shell assembly 220 and retention clip 240 are substantially similar to the shell assembly 20 and the retention clip 40 detailed above. For reasons of brevity only the differences between shell assembly 220 and retention clip 240 and the shell assembly 20 and the retention clip 40 will be detailed below. A proximal end portion 222 of the shell assembly 220 includes an annular surface 223 that defines a key slot 226 that extends through the proximal end 222a of the proximal end portion 222.

The retention clip 240 includes a key 247 having a leg 248 and a key end 249. The leg 248 is sized to slide freely through the key slot 226 and has a length L such that the key end 249 may be positioned against an inner surface of the shell assembly 220 and lugs 244 of the retention clip 240 may be positioned on an outer surface of the proximal end portion 222 of the shell assembly 220 as detailed below. The key end 249 is substantially T-shaped such that the key end 249 is inhibited from passing through the key slot 226 to prevent the retention clip 240 from disengaging the proximal end portion 222 of the shell assembly 220.

The retention clip 240 is attached to the shell assembly 220 by aligning the key 247 of the retention clip 240 with the key slot 226 of the shell assembly 220 and flexing the ends 242 of the retention clip 242 outwardly. The leg 248 of the key 247 is slid into the key slot 226 with the key end 249 positioned adjacent the inner surface of the proximal end portion 222 such that the lugs 244 of the retention clip 240 are positioned on the outer surface of the proximal end portion 222 of the shell assembly 220. When the key 247 is fully within the key slot 226, the retention clip 240 is pressed over the proximal end portion 220 until the lugs 244 are received within engagement openings 224 in a manner similar to that detailed above with respect to retention clip 40.

Figure 18:
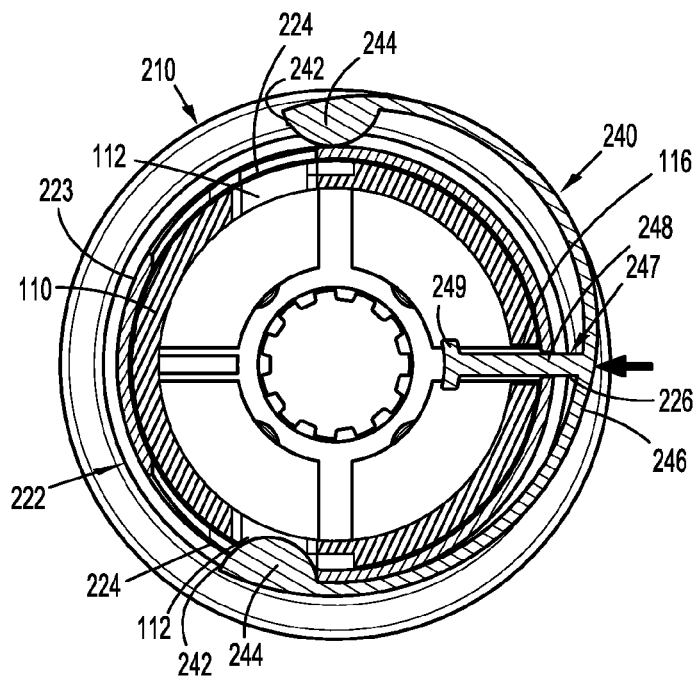
FIG. 18 is a rear cross-sectional view of the loading unit of FIG. 17 with the distal end of the adapter of FIG. 3 received within the proximal end portion of the loading unit.

The loading unit 210 is attached to an adapter (e.g., adapter 100) in a manner similar to loading unit 10 being attached to adapter 100 detailed above. After a surgical procedure is completed using loading unit 210, the loading unit 210 is detached from the adapter by engaging an end 242 of the retention clip 240 to remove one of the lugs 244 from a window (e.g., window 112) of the adapter. The end 242 may be moved until a body 246 of the retention clip 240 is permanently deformed as detailed above and then the other end 242 may be moved to remove the other lug 244 from the other window of the adapter. Alternatively, by permitting the leg 248 of the key 247 to pass freely through the key slot 226 to the key end 249, the first lug 244 may be removed from a window of the adapter and placed on the outer surface of the proximal end portion 222 between the engagement opening 224 and the key slot 226 with a portion of the key 247 passing through the key slot 226 as shown in FIG. 18. With the first lug 244 positioned on the outer surface of the proximal end portion 222, the other end 242 is then engaged to remove the other lug 244 from the other window 112 of the adapter and placed on the outer surface of the proximal end portion 222 between the engagement opening 224 and the key slot 226 with the key end 249 positioned adjacent the inner surface of the proximal end portion 222. It will be appreciated that during detachment of retention clip 240, the body 246 is resiliently flexed and not permanently deformed permitting reuse of the retention clip 240 and enabling a clinician to remove the loading unit 210 from an adapter without engaging both ends 242 simultaneously.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of securing a loading unit to a surgical instrument, the method comprising:
    inserting a distal end of the surgical instrument into a proximal end portion of the loading unit, the distal end of the surgical instrument flexing lugs of a retention clip passing through engagement openings defined in an annular surface of the loading unit outward as the distal end of the surgical instrument is received within the proximal end portion of the loading unit, the lugs received in windows defined in the distal end of the surgical instrument when the distal end of the surgical instrument is fully received within the proximal end portion of the loading unit to secure the loading unit to the surgical instrument.

2. The method according to claim 1, further comprising attaching the retention clip to the proximal end portion of the loading unit.

3. The method according to claim 2, wherein attaching the retention clip to the proximal end portion of the loading unit precedes inserting a distal end of the surgical instrument into the proximal end portion of the loading unit.

4. The method according to claim 2, wherein attaching the retention clip to the proximal end portion of the loading unit includes:
    inserting a key of the retention clip through a key slot defined in the annular surface of the loading unit; and
    positioning a body of the retention clip within an annular groove defined in the proximal end portion of the loading unit until each lug passes through a respective engagement opening through the annular surface.

5. The method according to claim 4, wherein inserting the key of the retention clip through the key slot includes press-fitting the key into the key slot.

6. The method according to claim 4, wherein inserting the key of the retention clip through the key slot includes positioning a key end of the key radially inward from the annular surface, the key end retaining the retention clip to the proximal end portion of the loading unit.

7. The method according to claim 1, further comprising aligning the distal end of the surgical instrument with the proximal end portion of the loading unit such that a key of the retention clip is aligned with a key way that extends through the distal end of the surgical instrument.

8. The method according to claim 7, wherein inserting the distal end of the surgical instrument into a proximal end portion of the loading unit includes sliding the key of the retention clip into the key way of the distal end of the surgical instrument.

* * * * *